US008436325B2

(12) United States Patent
Noda et al.

(10) Patent No.: US 8,436,325 B2
(45) Date of Patent: May 7, 2013

(54) SYNCHROTRON AND PARTICLE THERAPY SYSTEM USING THE SAME

(75) Inventors: Fumiaki Noda, Hitachi (JP); Kazuo Hiramoto, Hitachiota (JP); Takahiro Yamada, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/449,948

(22) Filed: Apr. 18, 2012

(65) Prior Publication Data

US 2012/0267543 A1 Oct. 25, 2012

(30) Foreign Application Priority Data

Apr. 19, 2011 (JP) .................................. 2011-092597

(51) Int. Cl.
*G21G 5/00* (2006.01)
(52) U.S. Cl.
USPC ................... 250/492.1; 250/492.2; 250/492.3
(58) Field of Classification Search ..... 250/492.1–492.3
See application file for complete search history.

(56) References Cited

U.S. PATENT DOCUMENTS 6,008,499 A 12/1999 Hiramoto et al.
6,087,670 A 7/2000 Hiramoto et al.

FOREIGN PATENT DOCUMENTS

JP 10-162999 A 6/1998

OTHER PUBLICATIONS

Furukawa et al.; "Design of Synchrotron at NIRS for Carbon Therapy Facility"; Proceeding of APAC 2004, Gyeongju, Korea; pp. 420-422.
Møller et al.; "A Novel Proton and Light Ion Synchrotron for Particle Therapy"; Proceedings of EPAC 2006, Edinburgh, Scotland; pp. 2305-2307.
Kang et al.; "Lattice Design of a Carbon-Ion Synchrotron for Cancer Therapy"; Proceedings of EPAC08, Genoa, Italy; 2008; pp. 1803-1805.

*Primary Examiner* — Michael Maskell
(74) *Attorney, Agent, or Firm* — Mattingly & Malur, PC

(57) ABSTRACT

Disclosed herein are provided an arrangement of devices suitable to downsize a synchrotron, a synchrotron using such an arrangement, and a particle therapy system using the synchrotron. In the synchrotron, a plurality of deflection magnets and a single defocusing quadrupole magnet are arranged between a first extraction deflector and a second extraction deflector. The defocusing quadrupole magnet is arranged between deflection magnets among the plurality of deflection magnets, a focusing quadrupole magnet is arranged on the side of an inlet of the first extraction deflector, and a focusing quadrupole magnet is arranged on the side of an outlet of the second extraction deflector.

14 Claims, 7 Drawing Sheets

SYNCHROTRON AND PARTICLE THERAPY SYSTEM USING THE SAME

BACKGROUND OF THE INVENTION

1. Field of the Invention

The present invention relates to an arrangement of devices suitable to downsize a synchrotron. The invention also relates to a synchrotron using such an arrangement and a particle therapy system using the synchrotron.

2. Description of the Related Art

In the aging society of recent years, as one of cancer treatments, a radiation treatment, which applies less load on a human body and enables the quality of life to be maintained at a high level after the treatment, has attracted attention. A particle therapy system that uses a charged particle beam (such as protons or carbon) accelerated by a synchrotron provides a high dose concentration to an affected part and has been expected as a promising system. The particle therapy system includes an injector, the synchrotron and an irradiation device. The injector supplies a charged particle beam to the synchrotron. The synchrotron accelerates the charged particle beam so that the speed of the charged particle beam becomes close to the speed of light. The irradiation device irradiates a patient with the charged particle beam extracted from the synchrotron on the basis of the position and shape of an affected part of the patient. There is a demand to reduce the size and cost of the particle therapy system in order to expand use of the particle therapy system.

As one of methods for extracting the beam from the synchrotron, there is an extraction method called a slow extraction method (resonance extraction method). The slow extraction method is different from a quick extraction method in which the entire charged particle beam is extracted during one circulation of the charged particle beam in the synchrotron. When the slow extraction method is used, the charged particle beam can be slowly extracted during a plurality of circulations of the charged particle beam in the synchrotron. The extracted beam is mainly used for a particle therapy or a physics experiment.

FIG. 4 illustrates a first example of a conventional synchrotron. A synchrotron 200 includes an injection deflection device 201 (SM, ESI), deflection magnets 202 (BM), focusing quadrupole magnets 203 (QF), defocusing quadrupole magnets 204 (QD), a radio frequency acceleration cavity 205 (RF-cavity), a resonance excitation multi-pole magnet 206 (SXFr, SXDr; only one resonance excitation multi-pole magnet is illustrated in FIG. 4), an extraction radio frequency device 207 (RF-KO), a first extraction deflector 208 (ESD) and a second extraction deflector 209 (SMI). The injection deflection device 201 causes a beam that is accelerated by a pre-accelerator 101 to be injected into the synchrotron 200. The deflection magnets 202 each deflect the injected beam and cause the beam to circulate in the synchrotron 200. The focusing quadrupole magnets 203 each cause the beam to stably circulate in the synchrotron 200 and focus the beam in a horizontal direction in order to prevent an increase in the size of the beam. The defocusing quadrupole magnets 204 each defocus the beam in the horizontal direction. The radio frequency acceleration cavity 205 accelerates and decelerates the beam. The resonance excitation multi-pole magnet 206 forms a separatrix for an oscillation (betatron oscillation) of the beam in order to cause the beam to be slowly extracted. The extraction radio frequency device 207 increases the amplitude of the oscillation of the beam and thereby leads the beam to the outside of the separatrix. The first extraction deflector 208 and the second extraction deflector 209 deflect the beam, change a path of the beam and cause the beam to be extracted from the synchrotron in order to introduce the accelerated and/or decelerated beam into an irradiation device.

In order to extract the beam from the synchrotron using the slow extraction method, the resonance excitation multi-pole magnet 206 excites resonance and forms the separatrix, and the extraction radio frequency device 207 increases the amplitude of the beam and thereby leads the beam to the outside of the separatrix. The amplitude of the beam that is led to the outside of the separatrix is further increased, and the beam propagates into the first extraction deflector 208. Then, the beam that propagates into the first extraction deflector 208 is deflected by the first extraction deflector 208, thereby being distanced from a beam that circulates in the synchrotron. The charged particle beam that is deflected by the first extraction deflector 208 is further deflected by the defocusing quadrupole magnet 204 (located on the downstream side of the first extraction deflector 208) toward the outer side of the synchrotron 200 in the horizontal direction. The charged particle beam that is deflected by the defocusing quadrupole magnet 204 toward the outer side of the synchrotron 200 in the horizontal direction passes through the deflection magnet 202 and is deflected by the focusing quadrupole magnet 203 (located on the downstream side of the defocusing quadrupole magnet 204) toward the inner side of the synchrotron 200 in the horizontal direction. Then, the charged particle beam is deflected by the second extraction deflector 209 toward the outer side of the synchrotron 200 in the horizontal direction and extracted from the synchrotron 200.

SUMMARY OF THE INVENTION

FIGS. 4 to 6 illustrate arrangements of main parts of synchrotrons described in "DESIGN OF SYNCHROTRON AT NIRS FOR CARBON THERAPY FACILITY", Proceedings of APAC 2004, p 420-422, Gyeongju, Korea, "A NOVEL PROTON AND LIGHT ION SYNCHROTRON FOR PARTICLE THERAPY", Proceedings of EPAC 2006, p 2305-2307 Edinburgh, Scotland, and "LATTICE DESIGN OF A CARBON-ION SYNCHROTRON FOR CANCER THERAPY", Proceedings of EPAC 2008, p 1803-1805, Genoa, Italy (hereinafter referred to as Non-Patent Documents 1 to 3). The synchrotron illustrated in FIG. 4 is described above as a conventional technique. As well as the synchrotron illustrated in FIG. 4, the The synchrotrons illustrated in FIGS. 5 and 6 each have a plurality of quadrupole magnets 203, 204 that are arranged between a first extraction deflector 208 (ESD described in Non-Patent Documents 1 and 3 and SS2 described in Non-Patent Document 2) and a second extraction deflector 209 (SM1 described in Non-Patent Documents 1 and 3 and SS4 described in Non-Patent Document 2) in order to prevent an increase in the size of a beam. In each of these cases, the number of devices is large. Thus, there is a limitation in reducing the size of the synchrotron. In addition, the extracted beam is deflected back to the inner side of the synchrotron (or to the side of a circulating beam) by the focusing quadrupole magnets 203 arranged between the first extraction deflector 208 and the second extraction deflector 209. In order to compensate for the deflection, it is necessary to set a deflection angle of the first extraction deflector 208 to a large angle. As the first extraction deflector 208, a device that is called an electrostatic deflector (ESD) (electrostatic extraction septum described in Non-Patent Document 2) is used in order to reduce beam loss. In order to increase a deflection angle per unit length of the electrostatic deflector, it is necessary to increase the intensity of an electric field. There is, however, a limitation to the intensity of the electric field in order to avoid discharge. Thus, in order to extract a charged particle beam with higher energy than protons or helium from the synchrotron, an electrostatic deflector that has a long length in a circumferential direction of the synchrotron and can deflect the beam at a sufficient angle needs to be arranged. This prevents the synchrotron from being downsized. As an invention that solves those problems, JP-A-10-162999 describes that defocusing quadrupole magnets 204 are arranged on inlet and outlet sides of a deflection magnet arranged between a first extraction deflector 208 and a second extraction deflector 209 as an example, as illustrated in FIG. 7. In this case, since the number of quadrupole magnets is increased, there is a limitation in downsizing the synchrotron. JP-A-10-162999 describes an example in which the deflection magnet is divided into magnets, a focusing quadrupole magnet 203 is arranged between the divided magnets, and defocusing quadrupole magnets 204 are arranged on the inlet side of an upstream-side magnet among the divided magnets and on the outlet side of a downstream-side magnet among the divided magnets. In this case, the number of devices is increased, and there is a disadvantage in downsizing the synchrotron.

An object of the present invention is to downsize a synchrotron by reducing the number of quadrupole magnets and reducing the length of an extraction deflector while suppressing an increase in the size of a beam. In addition, another object of the present invention is to provide a particle therapy system that includes the synchrotron.

In one aspect of the present invention, a plurality of deflection magnets 202 and a single defocusing quadrupole magnet 204 are arranged between a first extraction deflector 208 and a second extraction deflector 209, the single defocusing quadrupole magnet 204 is arranged between deflection magnets among the plurality of deflection magnets 204, and focusing quadrupole magnets 203 are arranged on the inlet side (upstream side) of the first extraction deflector 208 and on the outlet side (downstream side) of the second extraction deflector 209.

According to the one aspect of the present invention, the plurality of deflection magnets are arranged between the first extraction deflector 208 and the second extraction deflector 209. The single quadrupole magnet is arranged between the deflection magnets among the plurality of deflection magnets. The quadrupole magnets are arranged on the inlet side of the first extraction deflector 208 and on the outlet side of the second extraction deflector 209. Thus, the number of quadrupole magnets arranged between the first extraction deflector 208 and the second extraction deflector 209 can be reduced while an increase in the size of the beam is suppressed. This reduces a space in which devices are arranged. In addition, the single quadrupole magnet that is arranged between the deflection magnets among the plurality of deflection magnets (arranged between the first extraction deflector 208 and the second extraction deflector 209) is the defocusing quadrupole magnet. The quadrupole magnets that are arranged on the inlet side of the first extraction deflector 208 and on the outlet side of the second extraction deflector 209 are the focusing quadrupole magnets. Thus, an effect of deflecting the extracted beam toward the outer side of the synchrotron in a horizontal direction can be added, and there is no effect of deflecting the extracted beam (that has been deflected by the first extraction deflector 208) back to the side of a circulating beam by means of the quadrupole magnet. Thus, a deflection angle (kick angle) of the first extraction deflector 208 can be set to a small angle, and an incident angle of the beam on the second extraction deflector 209 can be set to a large angle. That is, the number of quadrupole magnets can be reduced and the first extraction deflector 208 and the second extraction deflector 209 can be downsized. As a result, the synchrotron can be downsized.

DESCRIPTION OF THE PREFERRED EMBODIMENTS

Embodiments of the present invention are described below with reference to the accompanying drawings.

First Embodiment

Figure 1:
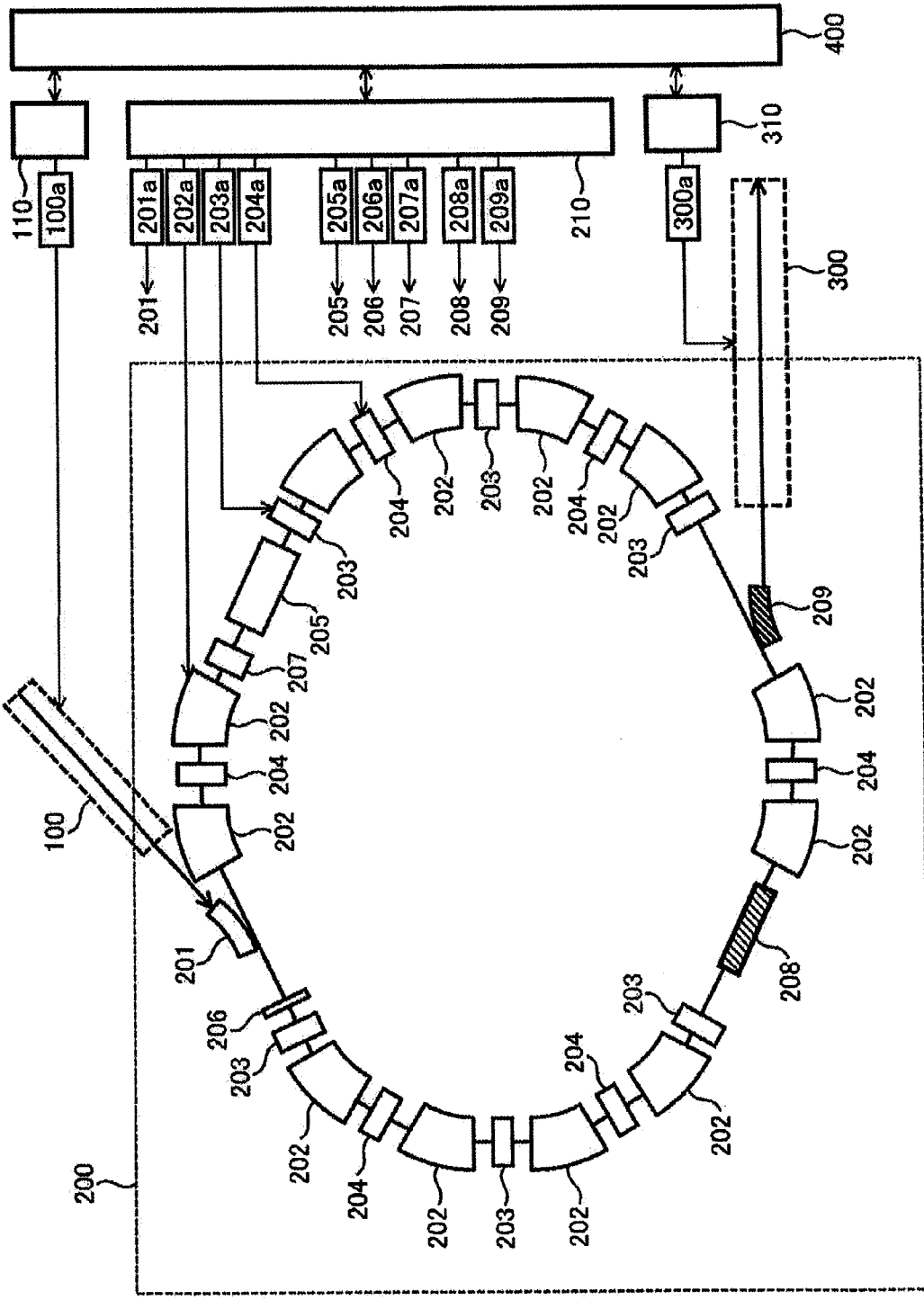
FIG. 1 is a diagram illustrating the configuration of a synchrotron according to a first embodiment of the present invention.

The configuration of a synchrotron according to a first embodiment of the present invention is described below with reference to FIG. 1.

A particle therapy system includes a beam injection system 100, a synchrotron 200 and a beam transport/irradiation system 300. The beam injection system 100 has a pre-accelerator and a transport system. The pre-accelerator accelerates a charged particle beam (hereinafter also referred to as beam) until the beam has energy that is sufficient for the beam to be injected into the synchrotron 200. The transport system transports the beam. The synchrotron 200 accelerates the injected beam until the beam has desired energy. The beam transport/irradiation system 300 transports the beam accelerated and extracted from the synchrotron 200 to a target to be irradiated and irradiates the target with the beam. In addition, the particle therapy system includes a control system (including an injection control device 110, a synchrotron control device 210 and a beam transport/irradiation system control device 310) and a central control device 400. The injection control device 110 controls the beam injection system 100 via a power source 100a thereof. The synchrotron control device 210 controls the synchrotron 200 via power sources 201a-209a thereof. The beam transport/irradiation system control device 310 controls the beam transport/irradiation system 300 via a power source 300a thereof. The central control device 400 controls the entire particle therapy system.

The synchrotron 200 includes an injection deflection device 201, deflection magnets 202, focusing quadrupole magnets 203, defocusing quadrupole magnets 204, a radio frequency acceleration cavity 205, a resonance excitation multi-pole magnet 206, an extraction radio frequency device 207, a first extraction deflector 208 and a second extraction deflector 209. The injection deflection device 201 causes the beam to be injected into the synchrotron 200. The deflection magnets 202 each deflect the injected beam. The focusing quadrupole magnets 203 each focus the beam. The defocusing quadrupole magnets 204 each defocus the beam. The radio frequency acceleration cavity 205 accelerates and decelerates the beam. The resonance excitation multi-pole magnet 206 forms a separatrix for an oscillation (betatron oscillation) of the beam. The extraction radio frequency device 207 increases the amplitude of the oscillation of the beam and thereby leads the beam to the outside of the separatrix. The first extraction deflector 208 and the second extraction deflector 209 deflect the beam, change a path of the beam and cause the beam to be extracted from the synchrotron 200.

As one of slow extraction methods for extracting the beam from the synchrotron, there is a diffusion resonance extraction method. In the diffusion resonance extraction method, the resonance excitation multi-pole magnet 206 excites resonance and forms the separatrix, and the extraction radio frequency device 207 increases the amplitude of the beam and thereby leads the beam to the outside of the separatrix. The amplitude of the beam that is led to the outside of the separatrix is further increased. Then, the beam propagates into the first extraction deflector 208. The first extraction deflector 208 has an effect of separating a beam to be extracted from the synchrotron 200 from a beam that circulates in the synchrotron 200. Thus, the thickness of a septum needs to be small as much as possible, and beam loss needs to be reduced as much as possible. In the first embodiment, an electrostatic deflector is used as the first extraction deflector 208. In the present embodiment, two deflection magnets and a single defocusing quadrupole magnet are arranged between the first extraction deflector 208 and the second extraction deflector 209 so that a separation of the extracted beam from the circulating beam at an inlet of the second extraction deflector 209 is ensured efficiently by a small deflection angle. The defocusing quadrupole magnet is arranged between the two deflection magnets in order to suppress an increase in the size of the circulating beam. A focusing quadrupole magnet 203 is arranged on the upstream side of the first extraction deflector 208, while a focusing quadrupole magnet 203 is arranged on the downstream side of the second extraction deflector 209 (on a path of the circulating beam).

In the present embodiment, the plurality of deflection magnets 202 are arranged between the first extraction deflector 208 and the second extraction deflector 209. The single quadrupole magnet 204 is arranged between two of the deflection magnets 202. The quadrupole magnet 203 is arranged on the upstream side of the first extraction deflector 208 (or the quadrupole magnet 203 and the first extraction deflector 208 are arranged in this order from the upstream side in a traveling direction of the beam that circulates in the synchrotron). The quadrupole magnet 203 is arranged on the downstream side of the second extraction deflector 209 (or the second extraction deflector 209 and the quadrupole magnet 203 are arranged in this order from the upstream side in the traveling direction of the beam that circulates in the synchrotron). In this configuration, the number of quadrupole magnets arranged between the first extraction deflector 208 and the second extraction deflector 209 can be reduced while an increase in the size of the beam is suppressed. Thus, a space in which devices are arranged can be reduced.

In the present embodiment, the single quadrupole magnet that is arranged between the deflection magnets 202 arranged between the first extraction deflector 208 and the second extraction deflector 209 is the defocusing quadrupole magnet 204. The quadrupole magnet that is arranged on the upstream side of the first extraction deflector 208 is the focusing quadrupole magnet 203. The quadrupole magnet that is arranged on the downstream side of the second extraction deflector 209 is the focusing quadrupole magnet 203. In this configuration, an effect of deflecting the extracted beam toward the outer side of the synchrotron in the horizontal direction can be added, and there is no effect of deflecting the extracted beam (that has been deflected by the first extraction deflector 208) back to the side of the circulating beam by means of the quadrupole magnet. Thus, the deflection angle (kick angle) of the first extraction deflector 208 can be set to a small angle and an incident angle of the beam on the second extraction deflector 209 can be set to a large angle. Thus, the number of quadrupole magnets can be reduced, while the first extraction deflector 208 and the second extraction deflector 209 can be downsized. As a result, the synchrotron can be downsized.

In the present embodiment, a distance between the focusing quadrupole magnet 203 (arranged on the upstream side of the first extraction deflector 208) and the defocusing quadrupole magnet 204 (arranged between the first extraction deflector 208 and the second extraction deflector 209) and a distance between the defocusing quadrupole magnet 204 (arranged between the first extraction deflector 208 and the second extraction deflector 209) and the focusing quadrupole magnet 203 (arranged on the downstream side of the first extraction deflector 209) can be set to equal to each other. If the distances are largely different from each other, the size of the beam increases in long regions located between the quadrupole magnets in general. In the present embodiment, since the distances are equal to each other, the number of quadrupole magnets arranged between the first extraction deflector 208 and the second extraction deflector 209 can be reduced while an increase in the size of the beam is suppressed. Thereby, the space in which the devices are arranged can be reduced. In addition, the quadrupole magnet that is arranged between the first extraction deflector 208 and the second extraction deflector 209 is the defocusing quadrupole magnet 204. Thus, the effect of deflecting the extracted beam toward the outer side of the synchrotron in the horizontal direction can be added, and there is no effect of deflecting the extracted beam (that has been deflected by the first extraction deflector 208) back to the side of the circulating beam by means of the quadrupole magnet. As a result, the kick angle of the first extraction deflector 208 can be set to a small angle and the incident angle of the beam on the second extraction deflector 209 can be set to a large angle.

Thus, the number of quadrupole magnets can be reduced, and the first extraction deflector 208 and the second extraction deflector 209 can be downsized. As a result, the synchrotron can be downsized.

In the present embodiment, the diffusion resonance extraction method is used as the slow extraction method. In addition, there are a method for extracting the beam by changing the size of the separatrix, a method in which a device that is called a betatron core is used (refer to Non-Patent Document 3), a method for causing the beam to contact a scatterer and thereby deflecting the beam, and the like. These methods are to lead the beam to the first extraction deflector 208. When any of the methods is used, the same effects as described above can be obtained.

In the present embodiment, the distance between the focusing quadrupole magnet 203 (arranged on the upstream side of the first extraction deflector 208) and the defocusing quadrupole magnet 204 (arranged between the first extraction deflector 208 and the second extraction deflector 209) and the distance between the defocusing quadrupole magnet 204 (arranged between the first extraction deflector 208 and the second extraction deflector 209) and the focusing quadrupole magnet 203 (arranged on the downstream side of the first extraction deflector 209) are equal to each other. The distances, however, may not be equal to each other. The distances may be different from each other as long as an increase in the size of the beam is in an acceptable range.

Second Embodiment

Figure 2:
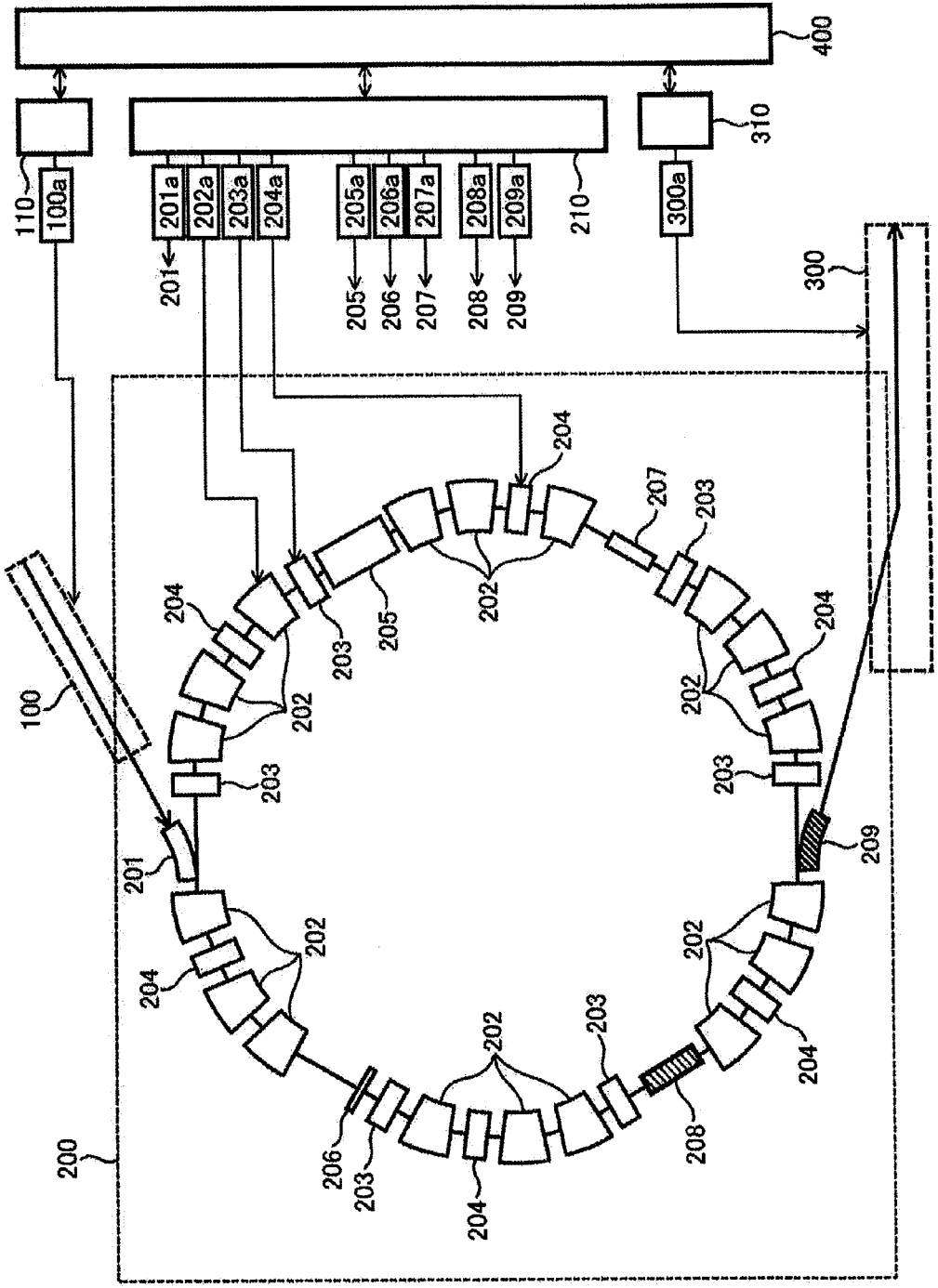
FIG. 2 is a diagram illustrating the configuration of a synchrotron according to a second embodiment of the present invention.

The configuration of a synchrotron according to a second embodiment of the present embodiment is described below with reference to FIG. 2.

In the present embodiment, three deflection magnets 202 and a single defocusing quadrupole magnet 204 are arranged between the first extraction deflector 208 and the second extraction deflector 209. In order to suppress an increase in the size of a beam circulating in the synchrotron, the defocusing quadrupole magnet 204 is arranged between a deflection magnet that is among the three deflection magnets 202 and arranged on the most upstream side in the traveling direction of the beam circulating in the synchrotron and a deflection magnet that is among the three deflection magnets 202 and arranged on the second most upstream side in the traveling direction of the beam circulating in the synchrotron. In addition, a focusing quadrupole magnet 203 is arranged on the upstream side of the first extraction deflector 208 (or the quadrupole magnet 203 and the first extraction deflector 208 are arranged in this order from the upstream side in the traveling direction of the beam circulating in the synchrotron). A focusing quadrupole magnet 203 is arranged on the downstream side of the second extraction deflector 209 (or the second extraction deflector 209 and the quadrupole magnet 203 are arranged in this order from the upstream side in the traveling direction of the beam circulating in the synchrotron).

In the present embodiment, the difference between a distance between the focusing quadrupole magnet 203 (arranged on the upstream side of the first extraction deflector 208) and the defocusing quadrupole magnet 204 (arranged between the first extraction deflector 208 and the second extraction deflector 209) and a distance between the defocusing quadrupole magnet 204 (arranged between the first extraction deflector 208 and the second extraction deflector 209) and the focusing quadrupole magnet 203 (arranged on the downstream side of the second extraction deflector 209) can be small, compared with an arrangement in which the defocusing quadrupole magnet 204 is arranged on the inlet side (upstream side) of the deflection magnet that is among the three deflection magnets 202 and arranged on the most upstream side (or compared with an arrangement in which the defocusing quadrupole magnet 204 is arranged on the outlet side (downstream side) of the deflection magnet that is among the three deflection magnets 202 and arranged on the most downstream side). In this configuration, the number of quadrupole magnets arranged between the first extraction deflector 208 and the second extraction deflector 209 can be reduced while an increase in the size of the beam is suppressed. Thus, a space in which devices are arranged can be reduced. The quadrupole magnet that is arranged between the first extraction deflector 208 and the second extraction deflector 209 is the defocusing quadrupole magnet 204. Thus, the effect of deflecting the extracted beam toward the outer side of the synchrotron can be added, and there is no effect of deflecting the extracted beam (that has been deflected by the first extraction deflector 208) back to the side of the circulating beam by means of the quadrupole magnet. Thus, the kick angle of the first extraction deflector 208 can be set to a small angle, and the incident angle of the beam on the second extraction deflector 209 can be set to a large angle.

The aforementioned effects make it possible to reduce the number of quadrupole magnets and downsize the first extraction deflector 208 and the second extraction deflector 209. As a result, the synchrotron can be downsized.

In the present embodiment, the single defocusing quadrupole magnet 204 (arranged between the first extraction deflector 208 and the second extraction deflector 209) is arranged between the deflection magnet that is among the three deflection magnets 202 and arranged on the most upstream side in the traveling direction of the beam circulating in the synchrotron and the deflection magnet that is among the three deflection magnets 202 and arranged on the second most upstream side in the traveling direction of the beam circulating in the synchrotron. The single defocusing quadrupole magnet 204 that is arranged between the first extraction deflector 208 and the second extraction deflector 209 may be arranged between the deflection magnet that is among the three deflection magnets 202 and arranged on the second most upstream side in the traveling direction of the beam circulating in the synchrotron and the deflection magnet that is among the three deflection magnets 202 and arranged on the most downstream side in the traveling direction of the beam circulating in the synchrotron.

Third Embodiment

Figure 3:
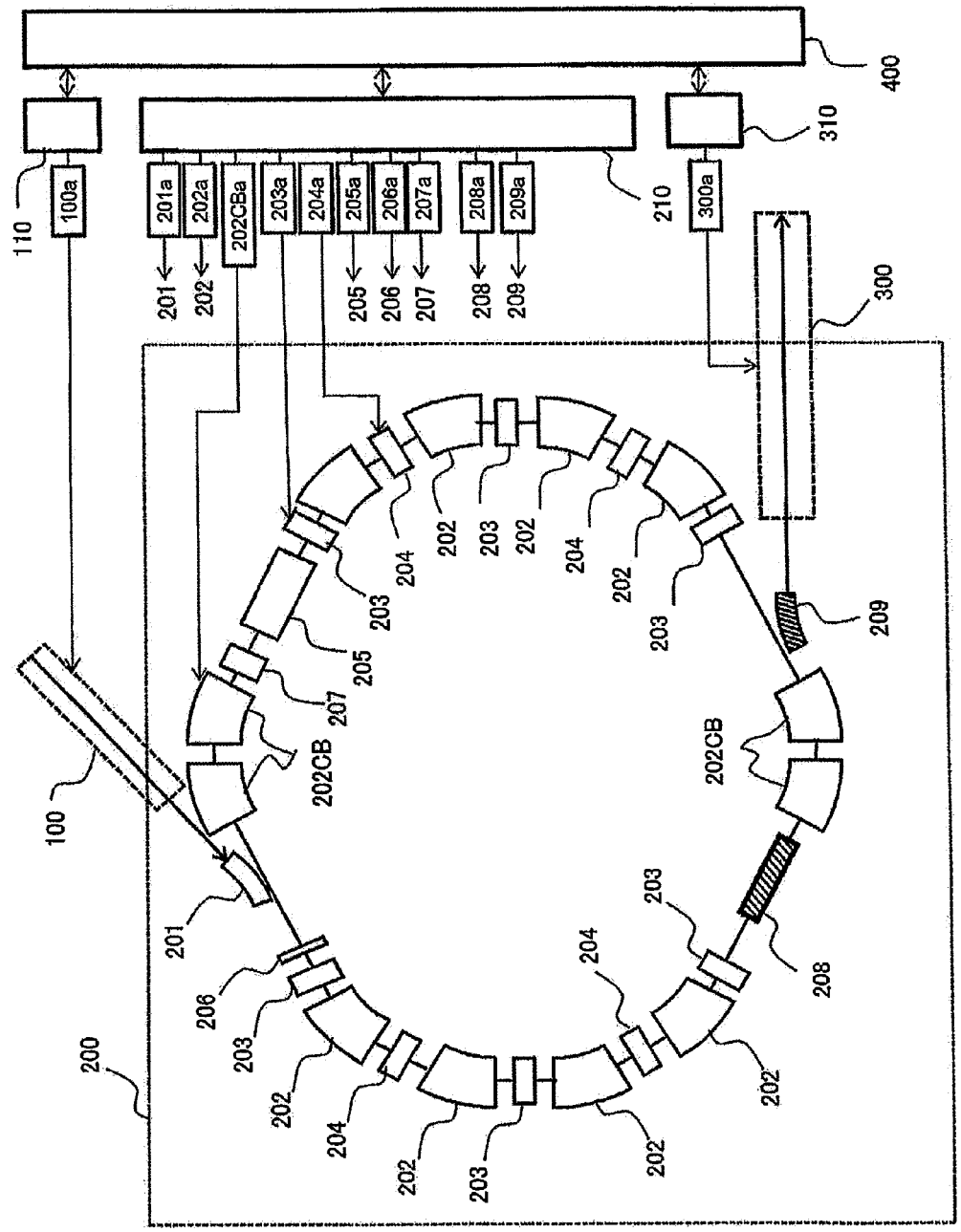
FIG. 3 is a diagram illustrating the configuration of a synchrotron according to a third embodiment of the present invention.
Figure 4:
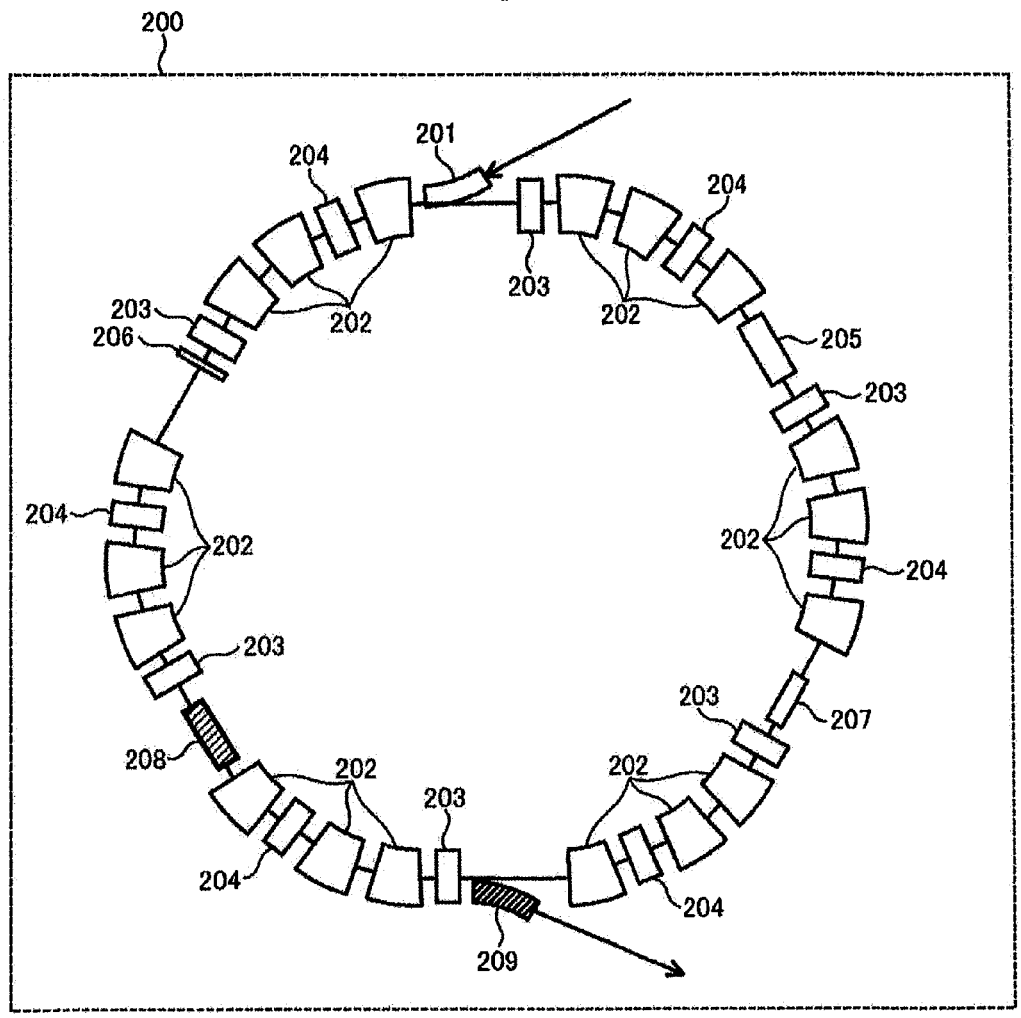
FIG. 4 is a diagram illustrating the configuration of a synchrotron according to a first example of a conventional technique.
Figure 5:
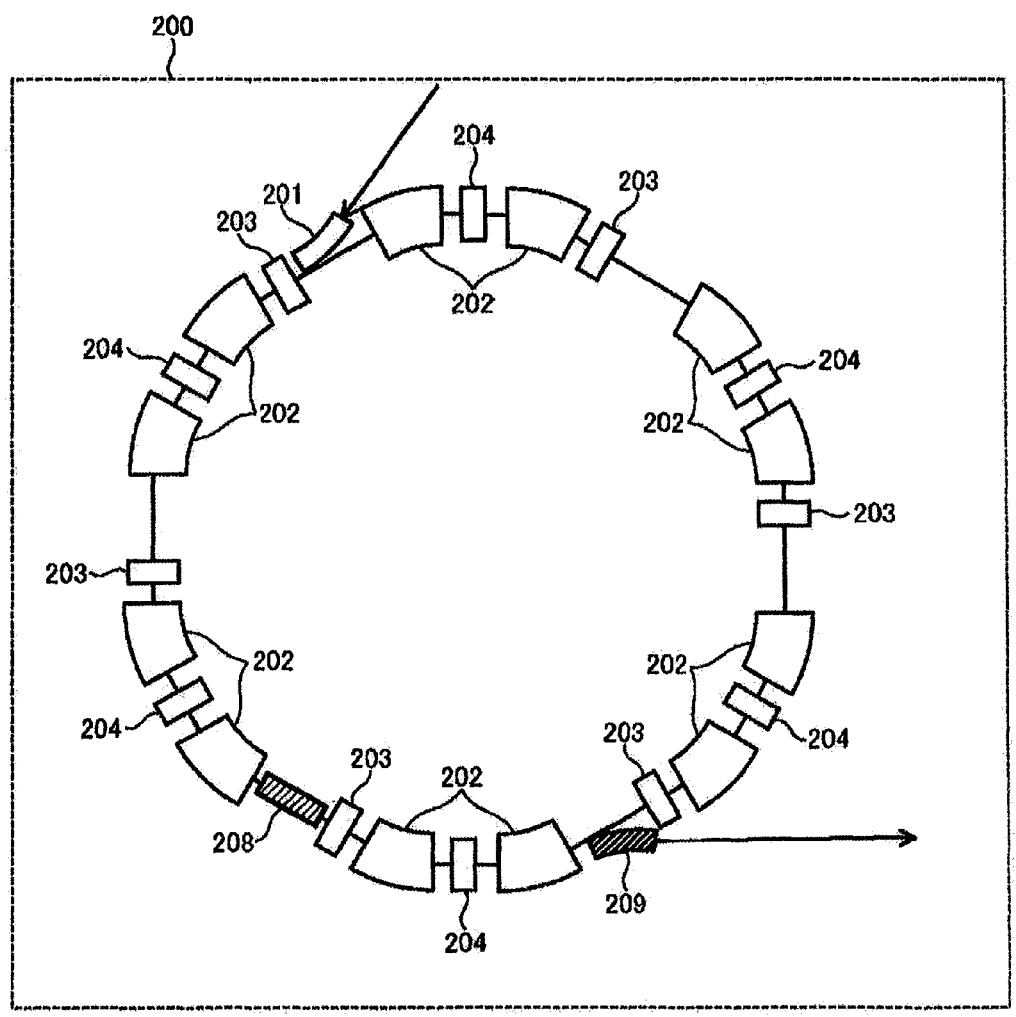
FIG. 5 is a diagram illustrating the configuration of a synchrotron according to a second example of the conventional technique.
Figure 6:
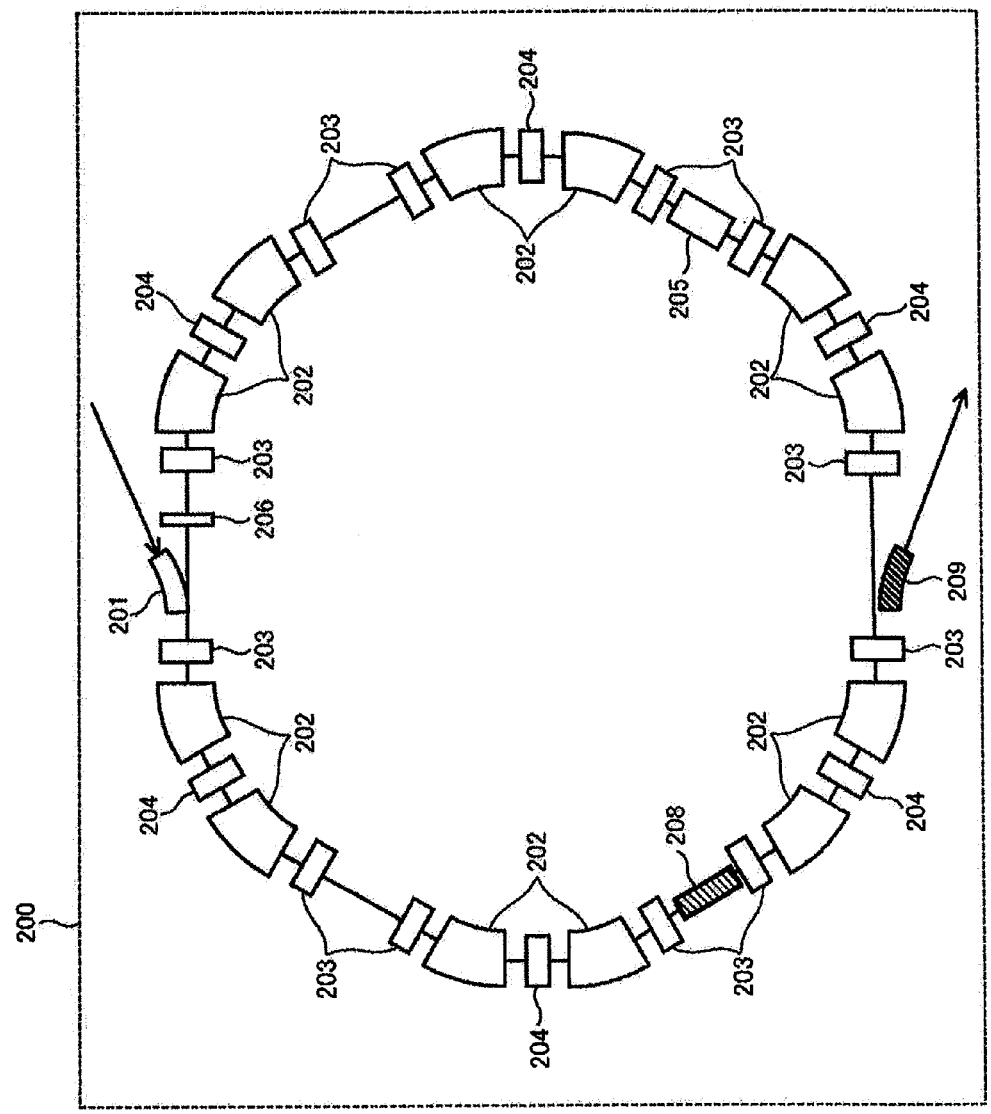
FIG. 6 is a diagram illustrating the configuration of a synchrotron according to a third example of the conventional technique.
Figure 7:
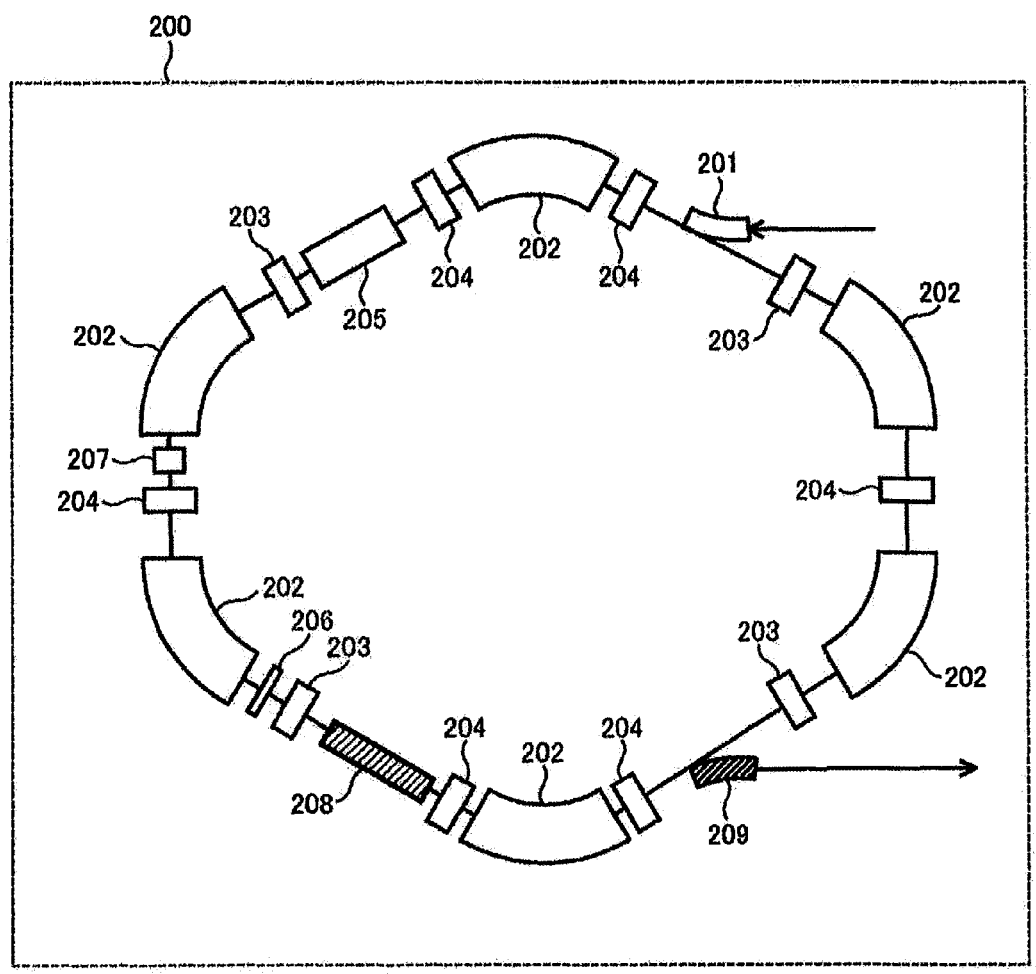
FIG. 7 is a diagram illustrating the configuration of a synchrotron according to a fourth example of the conventional technique.

The configuration of a synchrotron according to a third embodiment of the present invention is described below with reference to FIG. 3.

In the present embodiment, a combined function magnet or combined function magnets (n-indexed magnet) 202CB are arranged between the first extraction deflector 208 and the second extraction deflector 209. The combined function magnets 202CB each have a defocusing quadrupole function obtained by combining the function of the deflection magnet with the function of the defocusing quadrupole magnet.

In the present embodiment, since the combined function magnet 202CB has the defocusing quadrupole function, the effect of deflecting the extracted beam toward the outer side of the synchrotron can be added and there is no effect of deflecting the extracted beam (that has been deflected by the first extraction deflector 208) back to the side of the circulating beam by means of the quadrupole magnet. Thus, the kick angle of the first extraction deflector 208 can be set to a small angle, and the incident angle of the beam on the second extraction deflector 209 can be set to a large angle.

The aforementioned effects make it possible to reduce the number of quadrupole magnets and downsize the first extraction deflector 208 and the second extraction deflector 209. As a result, the synchrotron can be downsized.

In the third embodiment described above, a combined function magnet or combined function magnets 202CB are arranged between the first extraction deflector 208 and the second extraction deflector 209. Alternatively, for instance, a combined function magnet and a deflection magnet may be arranged between the first extraction deflector 208 and the second extraction deflector 209. Such a modified embodiment also provides the same advantages as the third embodiment.

What is claimed is:
1. A synchrotron that accelerates and decelerates a charged particle beam that circulates in the synchrotron, comprising:

a first extraction deflector and a second extraction deflector that are used to extract the accelerated or decelerated beam from the synchrotron;

a plurality of deflection magnets and a first single quadrupole magnet that are arranged between the first and second extraction deflectors, the first single quadrupole magnet being arranged between any deflection magnets among the plurality of deflection magnets;

a second quadrupole magnet that is arranged on the upstream side of the first extraction deflector in a traveling direction of the charged particle beam on a path of the circulating charged particle beam; and a third quadrupole magnet that is arranged on the downstream side of the second extraction deflector in the traveling direction of the charged particle beam on the path of the circulating charged particle beam.

2. The synchrotron according to claim 1,
wherein the first quadrupole magnet is a defocusing quadrupole magnet, and the second quadrupole magnet and the third quadrupole magnet are focusing quadrupole magnets.

3. The synchrotron according to claim 1,
wherein the plurality of deflection magnets arranged between the first and second extraction deflectors are a first deflection magnet and a second deflection magnet, and the first deflection magnet, the first quadrupole magnet and the second deflection magnet are arranged in this order from the upstream side in the traveling direction of the charged particle beam.

4. The synchrotron according to claim 1,
wherein the plurality of deflection magnets arranged between the first and second extraction deflectors are a first deflection magnet, a second deflection magnet and a third deflection magnet, and the first deflection magnet, the first quadrupole magnet, the second deflection magnet and the third deflection magnet are arranged in this order from the upstream side in the traveling direction of the charged particle beam.

5. The synchrotron according to claim 1,
wherein the plurality of deflection magnets arranged between the first and second extraction deflectors are a first deflection magnet, a second deflection magnet and a third deflection magnet, and the first deflection magnet, the second deflection magnet, the first quadrupole magnet and the third deflection magnet are arranged in this order from the upstream side in the traveling direction of the charged particle beam.

6. The synchrotron according to claim 1,
wherein a combined function magnet is used instead of the deflection magnet and the first quadrupole magnet that are arranged between the first and second extraction deflectors.

7. The synchrotron according to claim 6,
wherein the second quadrupole magnet and the third quadrupole magnet are focusing quadrupole magnets.

8. A particle therapy system comprising:
the synchrotron according to claim 1, and
a beam transport/irradiation system that transports the charged particle beam extracted from the synchrotron to a target and irradiates the target with the charged particle beam.

9. A particle therapy system comprising:
the synchrotron according to claim 2, and
a beam transport/irradiation system that transports the charged particle beam extracted from the synchrotron to a target and irradiates the target with the charged particle beam.

10. A particle therapy system comprising:
the synchrotron according to claim 3, and
a beam transport/irradiation system that transports the charged particle beam extracted from the synchrotron to a target and irradiates the target with the charged particle beam.

11. A particle therapy system comprising:
the synchrotron according to claim 4, and
a beam transport/irradiation system that transports the charged particle beam extracted from the synchrotron to a target and irradiates the target with the charged particle beam.

12. A particle therapy system comprising:
the synchrotron according to claim 5, and
a beam transport/irradiation system that transports the charged particle beam extracted from the synchrotron to a target and irradiates the target with the charged particle beam.

13. A particle therapy system comprising:
the synchrotron according to claim 6, and
a beam transport/irradiation system that transports the charged particle beam extracted from the synchrotron to a target and irradiates the target with the charged particle beam.

14. A particle therapy system comprising:
the synchrotron according to claim 7, and
a beam transport/irradiation system that transports the charged particle beam extracted from the synchrotron to a target and irradiates the target with the charged particle beam.

\* \* \* \* \*